United States Patent [19]

Vallana et al.

[11] Patent Number: 5,454,838
[45] Date of Patent: Oct. 3, 1995

[54] METHOD AND A DEVICE FOR MONITORING HEART FUNCTION

[75] Inventors: Franco Vallana; Bruno Garberoclio, both of Turin, Italy

[73] Assignee: Sorin Biomedica S.p.A., Saluggia, Italy

[21] Appl. No.: 97,083

[22] Filed: Jul. 26, 1993

[30] Foreign Application Priority Data

Jul. 27, 1992 [IT] Italy .................................. TO92A0646

[51] Int. Cl.⁶ .................................................. A61N 1/362
[52] U.S. Cl. .................................. 607/19; 607/6; 607/120; 128/695 R; 128/774
[58] Field of Search ............................ 607/19, 20, 119, 607/120, 122, 6; 128/695, 696, 713, 774

[56] References Cited

U.S. PATENT DOCUMENTS

| | | | |
|---|---|---|---|
| 3,663,932 | 5/1972 | Mount et al. | 340/1 R |
| 3,853,462 | 12/1974 | Smith . | |
| 3,986,828 | 10/1976 | Hoffman, Jr. et al. . | |
| 4,047,252 | 9/1977 | Liebig et al. . | |
| 4,193,137 | 3/1980 | Heck . | |
| 4,209,859 | 7/1980 | Hoffman . | |
| 4,301,809 | 11/1981 | Pinchak | 128/695 |
| 4,360,031 | 11/1982 | White | 607/120 |
| 4,676,253 | 6/1987 | Newman et al. | 128/713 X |
| 4,763,646 | 8/1988 | Lekholm . | |
| 4,917,115 | 4/1990 | Flammang et al. | 607/19 |
| 4,989,611 | 2/1991 | Zanetti et al. . | |
| 5,243,976 | 9/1993 | Ferek-Petric et al. | 607/19 X |
| 5,261,418 | 11/1993 | Ferek-Petric | 607/126 |
| 5,271,392 | 12/1993 | Ferek-Petric | 607/14 |
| 5,304,208 | 4/1994 | Inguaggiato et al. | 607/17 |

FOREIGN PATENT DOCUMENTS

| | | |
|---|---|---|
| 021800 | 4/1987 | European Pat. Off. . |
| 0383732 | 6/1990 | European Pat. Off. . |
| 0495293 | 7/1992 | European Pat. Off. . |
| 0515319 | 11/1992 | European Pat. Off. . |
| WO8701947 | 4/1987 | WIPO . |

OTHER PUBLICATIONS

Tiny Accelerometer Chip For Heart Implantation (Translation) Nachrichten Elecktronik. vol. 33, No. 2, Feb. 1979.

*Primary Examiner*—Lee S. Cohen
*Assistant Examiner*—Jeffrey R. Jastrzab
*Attorney, Agent, or Firm*—Popovich & Wiles

[57] ABSTRACT

Heart function is monitored by monitoring the momentum or velocity of the heart masses, preferably by means of a sensor implanted in the heart mass.

55 Claims, 3 Drawing Sheets

METHOD AND A DEVICE FOR MONITORING HEART FUNCTION

FIELD OF THE INVENTION

In general, the present invention addresses the problem of monitoring heart function.

Correct monitoring of heart function is important in order to be able to produce, for example:

systems for monitoring the behaviour of the cardiocirculatory system and of the heart muscle, particularly for diagnostic and therapeutic purposes, and monitoring devices which can be implanted for diagnostic and therapeutic purposes, possibly in conjunction with heart stimulators (pacemakers), particularly of the so-called "rate responsive" type, in which the characteristics of the stimulation activity can be varied in dependence on one or more parameters related to the physical activity of the person wearing the pacemaker, and with defibrillators.

Naturally, the possible fields of use mentioned above should in no way be interpreted in a limiting sense.

DESCRIPTION OF THE PRIOR ART

Over the years, various tecnhiques have been proposed for solving the problem of monitoring heart function.

For example, many techniques are based on the monitoring of electrical parameters of the activity of the heart. For example, this applies to electrocardiographic (ECG) equipment and to many pacemakers currently produced. The main disadvantage of these solutions is that the electrical parameters detected provide a very incomplete and, in many cases, inadequate description of the behaviour of the heart and of its functioning.

Other solutions provide for the use of sensors for monitoring chemical parameters: however, these solutions suffer from the main disadvantage that their operation is based on surface phenomena so that after a fairly short period of use they may no longer be capable of ensuring correct operation: this excludes the use of these solutions, for example, if the sensor is to be made suitable for implantation in the wearer's body for a long time.

Other solutions are based on techniques such as echocardiography, cardiac catheterization, and seismographic auscultation of the cardiac tones (see, for example, patent No. U.S. Pat. No. 4,989,611 in this connection). These techniques have the disadvantage that they are usually suitable only for interventions of short duration which can be performed only in acute phases. Moreover, the results of the monitoring are usually fairly approximate.

Finally, there are known solutions in which quantities derived directly from the measurement of ventricular pressure or, in general, quantities related to the contractility of the heart are used as parameters indicative of heart function. All these solutions have the disadvantage that, as an essential requisite for correct operation, they require the sensors to be able to remain permanently exposed to the effect of the parameter monitored: this is difficult to ensure, particularly when the sensor may interact with the body tissues so as to hinder or even prevent correct operation. It is very difficult, if not impossible, particularly when the sensors concerned are to be connected directly to the pulsating wall of the heart, to correlate the signal produced thereby (which is indicative primarily of the radial contractile activity of the heart muscle) to the essential fluido-dynamic parameters of the behaviour of the heart.

In fact, it should not be forgotten that the main function required of heart muscle is to act as a pump to bring about the movement of the blood within the cardiocirculatory system with predetermined flows and flow-rates.

For clarity, it should also be noted that the foregoing relates primarily to the monitoring of heart function: this monitoring action should not be confused with another, often related, function, that is, the monitoring of the physical activity or the metabolic needs of the patient: this field is the subject of intense research activity, to which numerous patent documents such as, for example, European Application EP-A-0 383 732 bear witness.

OBJECTS AND SUMMARY OF THE INVENTION

The object of the present invention is to provide a solution which enables heart function to be monitored correctly and which radically overcomes the problems of the solutions of the prior art.

According to the present invention, this object is achieved by virtue of a method and a device for monitoring heart function having the specific characteristics recited in the following claims.

As already stated, the solution according to the invention is suitable for application of a wholly general character, particularly as regards the production of diagnostic and/or therapeutic systems, possibly in conjunction with pacemakers and defibrillators. Naturally, those listed are only some of the possible fields of use of the invention.

The invention will now be described, purely by way of non-limiting example, with reference to the appended drawings, in which.

THEORETICAL PRINCIPLES OF THE INVENTION

By way of premise, it is considered useful to mention some theoretical principles upon which the invention is based. In fact, the invention provides for the use of the momentum and/or velocity of the heart masses, as well as the variations thereof over time, as primary parameters for identifying, detecting and monitoring heart activity.

As a first approximation, the heart and the connected vascular system may be considered as an isolated system in which movements of muscular and fluid masses take place in definite cycles and at definite intervals. The total mass is constant and is distributed within a volume which coincides approximately with the heart muscle and the main vessels.

At any moment, in the absence of external forces, the total momentum Q of the system is zero; this quantity is given by:

$$Q = \int_V \rho(r) \cdot u(r) \, dV \qquad \text{(I)}$$

in which $\vec{u}(\vec{r})$ represents the velocity of the mass contained in the volume element dV, in which $\rho(\vec{r})$ is the density at the generic point $\vec{r}$ and the integral is extended to the volume V containing the system.

The movement of a certain mass must correspond to a movement of other masses which renders the total momentum zero.

Thus, considering, for example, the systolic phase, if $m_1 \cdot \vec{v}_1$ represents the momentum resulting from the discharge of blood, the heart mass as a whole will have an equal and opposite momentum $m_2 \vec{v}_2$, that is $$m_2 \vec{v}_2 = -m_1 \vec{v}_1 \qquad \text{(II)}$$

The velocity $\vec{v}_2$ of the centre of masses of the heart mass, for example, is consequently a function of the velocity of the blood and of the mass of blood discharged.

Moreover, if, for example, a ventricular chamber (a subsystem) from which a quantity of blood is expelled within a certain period is considered, the following equation applies:

$$F_t = M \frac{dv}{dt} - u \frac{dM}{dt} \qquad \text{(III)}$$

in which $\vec{F}_t$ is the external force acting on the subsystem, M is the variable mass of the subsystem, $\vec{v}$ is the velocity of its centre of the masses and $\vec{u}$ the flow velocity relative to the centre of masses of the subsystem.

Figure 1:
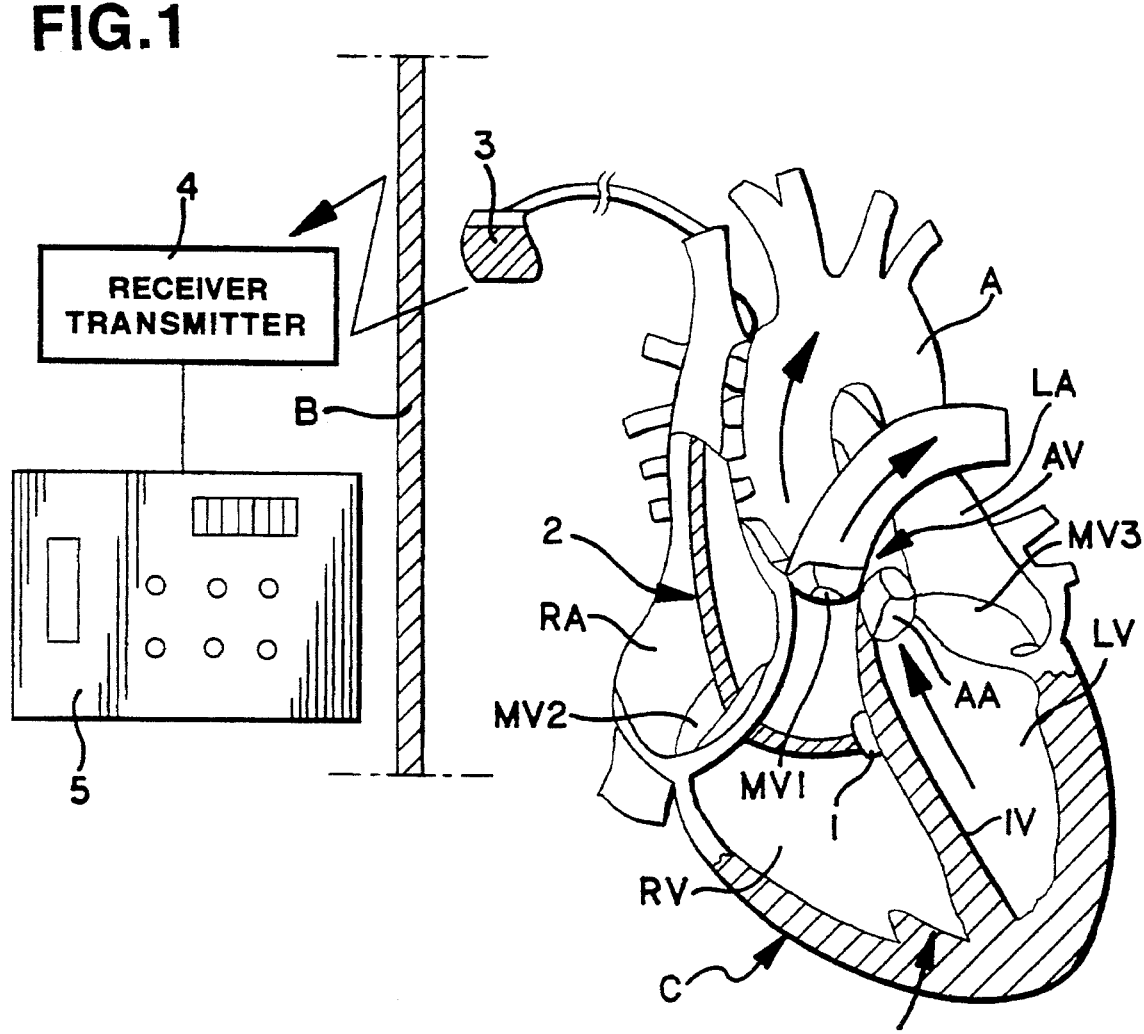
FIG. 1 shows schematically a possible configuration of a device operating according to the invention.
Figure 2:
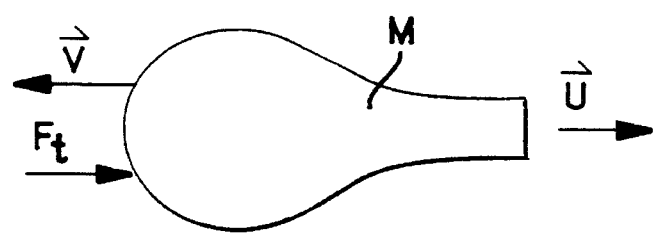
FIG. 2 is a diagram showing the physical principle upon which the invention is based, and FIG. 3 comprises three graphs, one above another, indicated a), b) and c), indicative of the behaviour of various heart-function monitoring signals.

In this particular case, if the mono-directional model of FIG. 2 is considered as a first approximation, it may be stated simply that:

$$F_t = M \frac{dv}{dt} - u^2 \Sigma \rho \qquad \text{(IV)}$$

in which $\epsilon$ is the cross-section of the discharge orifice and $\rho$ is the density of the blood.

In this case, $\vec{F}_t$ represents a force acting on the ventricular chamber which causes a retrograde acceleration and hence a movement; in reality, this movement is opposed and damped by the resilient biasing forces exerted by the tissues surrounding and supporting the heart.

More generally, it is found that the velocity of the blood discharged and the mass discharged are functions of the velocity of the system and of the external forces applied. Naturally, the phenomena which occur in the circulatory system are more complex and difficult to describe; however, for the purposes of the present invention it is necessary neither to seek a description of the physical model, nor to define the system under examination precisely.

In fact, it follows from the basic laws set out above and from the fact that the individual events of the heart cycle are separated in time and take place in ways which are known from physiology, that for each individual event there is:

a direction along which the component of the momentum corresponding to the event is substantially directed within the time interval considered, and an element of heart volume which moves in the direction specified substantially like the centre of the masses of the subsystem involved in the event.

If the position, the velocity, or the acceleration of the element in the direction indicated is measured by a transducer as a function of time (the three quantities being correlated by integration and differentiation operations) these are functions of the velocity and of the mass of blood in movement as well as of the resilient biasing forces.

Variations in the characteristics of each individual event in comparison with normal situations, modifications of the transportation dynamics and the pumping of blood, and hence diagnostic and clinical monitoring signals can consequently be detected from a record which gives one of the mechanical quantities mentioned, or a quantity derived therefrom, as a function of time.

DETAILED DESCRIPTION OF AN EMBODIMENT OF THE INVENTION

In the drawing, the heart muscle is generally indicated C, the left ventricle LV and the right ventricle RV thereof being shown specifically, separated by the interventricular septum IV.

The so-called atrioventricular septum which separates the two ventricles LV and RV from the respective atria LA and RA is generally indicated AV. The aorta which branches out from the left ventricle through the aortic valve AA is indicated A. The other valves of the heart muscle are indicated MV1 (the pulmonary valve), MV2 (the tricuspid valve) and MV3 (the mitral valve) respectively.

A mechanical/electrical sensor for implantation is generally indicated 1. In the embodiment illustrated, the sensor 1 is located on the interventricular septum IV in a position near the atrioventricular septum AV. It is introduced into the right ventricle RV and kept in contact with the interventricular septum IV by a catheter 2 which extends through the upper vena cava and the tricuspid valve MV2 to reach a supply/processing module 3 which is preferably implanted in the patient's body. The condition in which it is implanted in the body is shown schematically by means of the cutaneous barrier, indicated B, separating the portion of the system which is implanted in the body from any accessory elements such as a receiver/transmitter module 4 and a signal analyser 5 situated outside the patient's body.

The use of the transmitter-receiver module 4 and of the analyser 5 is generally envisaged when the system according to the invention is used for diagnostic purposes, that is, for monitoring the wearer's heart function externally.

When the solution according to the invention is used in combination with a heart stimulator (a pacemaker) or with a defibrillator which can be implanted, the module 3 usually comprises transmitter/receiver means which can transmit signals indicative of the heart activity monitored to the exterior, towards the module 4, and can also receive function-programming signals from the exterior, also by means of the module 4.

This is all in accordance with criteria widely known in the art which do not need to be described in detail herein and, moreover, are not relevant for the purposes of putting the invention into practice: this relates, in particular, to the methods adopted for the transcutaneous transmission of the signals between the modules 3 and 4. In particular, this transmission may take place by means of electromagnetic waves, ultrasound waves, or other suitable vectors.

Naturally, for use in combination with a pacemaker or a defibrillator, it is also possible to do without the transcutaneous transmission. In this case, the system is independent and autonomous and wholly implanted in the wearer's body.

The main characteristic of the sensor 1 used in the device according to the invention is that it is made sensitive primarily to the momentum (and hence, in particular, to the velocity) of the heart mass as a whole, seen theoretically as a vectorial quantity concentrated at the centre of masses of the heart mass. Theoretically, since, as is well known, the dynamic behaviour of the heart mass is such as to give rise to continuous variations in the position of its instantaneous centre of mass.

It is usually preferable to position the implanted sensor 1 on the interventricular septum IV and/or on the atrioventricular septum AV, particularly as far as its application to systems for the diagnostic monitoring of heart activity is concerned. The interventricular and atrioventricular septa IV and AV are in fact the sites within the heart mass which are least exposed to the actual contractile activity of the external walls of the heart muscle. If the momentum or velocity of the heart mass is to be monitored as the main parameter of the activity of the heart, positioning in regions which are not subject to the beating of the heart itself is thus generally preferable.

On the other hand, for use in combination with a pacemaker or a defibrillator, it may be advantageous (according to a known solution) for the sensor also to be able to perform the electrical stimulation function. In this case, positioning on the heart wall the contractile activity of which is to be stimulated (typically the wall of the right ventricle RV) is to be considered greatly preferable.

The monitoring of the sensor then tends to be disturbed by the signals induced by the contractile activity of the heart wall, particularly the signals which express the acceleration of the heart wall in a generally radial direction. In this case, the processing device 3 usually has filter means which can clear the signal produced by the sensor 1 of the components which relate to the physiological parameters considered to be sources of disturbance.

It is also possible to consider using, as the sensor, a sensor with spatially non-uniform monitoring characteristics and hence, if it is to be implanted on a ventricular wall, the use of a sensor the direction of maximum sensitivity of which does not coincide with the direction of radial contraction, but, on the contrary, coincides with the general direction (approximately tangential) in which the net pumping action of the blood masses is brought about by the portion of the heart muscle concerned.

It is also possible to consider the use of several sensors the output signals of which are used in combination so as to obtain a final signal which is free of disturbance components.

As far as the production of the sensor 1 is concerned, the use of various technological solutions may be considered: however, all these make use of sensors available in the art.

A family of sensors which has been found particularly advantageous for this purpose is the accelerometric sensors, for example, based on piezoelectric ceramics, possibly integrated with seismic masses.

In this case, the signal relating to the velocity of the heart mass (and the respective momentum signal) can be obtained from the accelerometric signal produced by the sensor 1 by integrator means (analog or digital) in the signal-processing unit 3.

Amongst other things, the accelerometric sensors of the type specified above have the advantage that they can conveniently be produced with one directional component having more accentuated sensitivity, consequently enabling the undesired components (radial acceleration) already to be excluded when the signal is detected.

Naturally, the sensor 1 may also be produced by different technologies and may thus be consituted by a piezoresistive, capacitive, inductive, magnetic (for example, Hall-effect) sensor, or the monitoring may be achieved by evaluating variations in the impedance of a conductive fluid which deforms as a result of the acceleration, or by flow-rate measurements. In particular, as already stated, the use of several sensors in combination: for example, an accelerometric sensor and a flow-rate sensor, may be considered.

As well as enabling the sensor 1 to be introduced into the implant position within the heart muscle and enabling the monitoring signals of the sensor 1 to be picked up by the processing device 3, the catheter 2 also enables the electrical stimulation pulses to be conveyed towards the sensor/ electrode, if the sensor 1 is also used for performing the stimulation fuction. This is all in accordance with criteria which are widely known in the art and do not need to be described specifically in the present description.

The processing/transmission module 3 may be produced according to the microeletronic technologies normally used for producing the units for piloting the pacemakers in current use.

Figure 4:
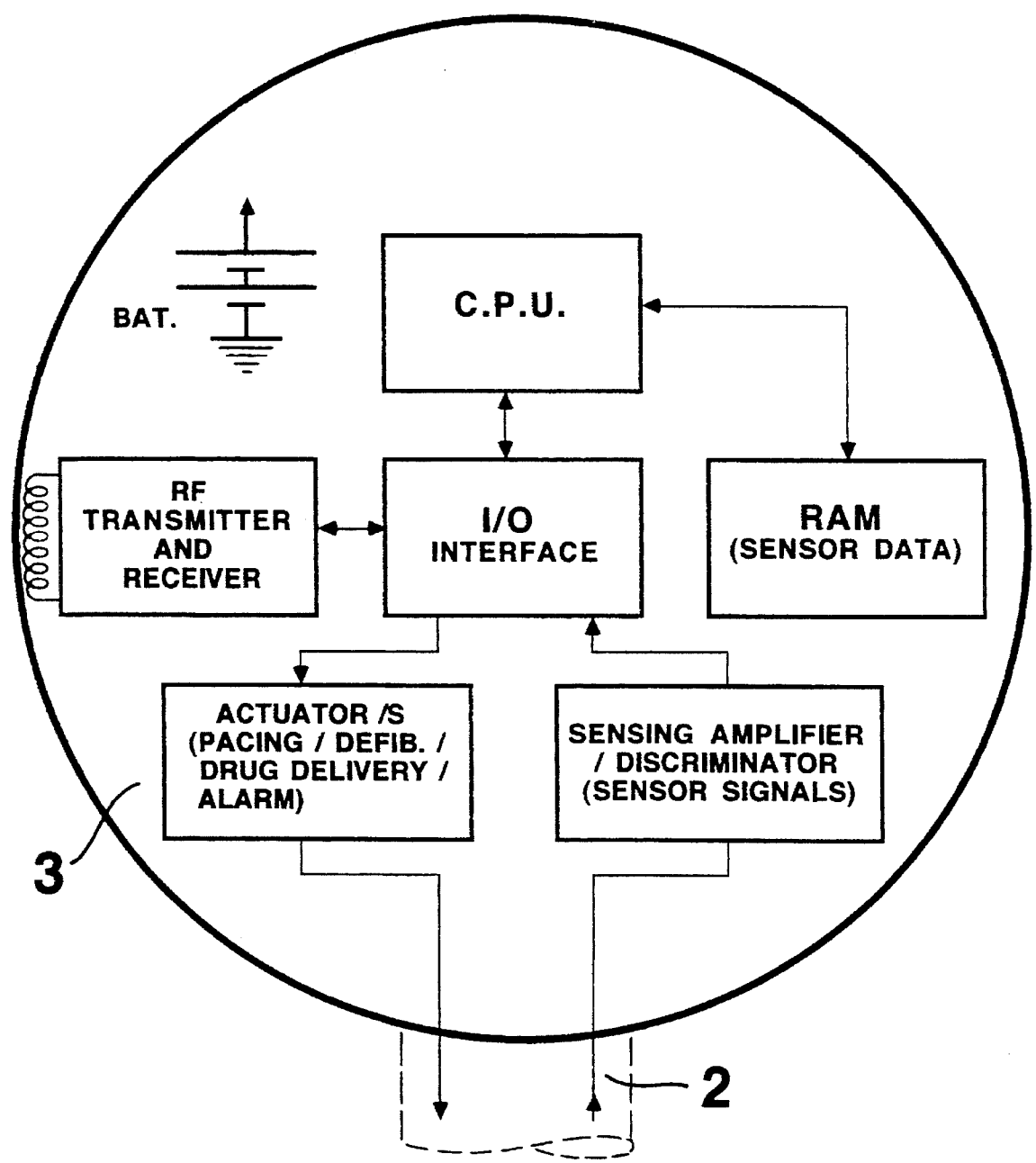
FIG. 4 is an extended block diagram showing components of the processing device according to the invention.

In particular, the module 3, FIG. 4, usually comprises an input interface for picking up the signals coming from the sensor 1 possibly converting them from analog to digital form and subsequently processing them in order to obtain a velocity (momentum) signal which is adequately cleared of spurious components. For example, this result can be obtained by integrating an accelerometric signal which is cleared of the acceleration components which are not relevant for the purposes of identifying the velocity of the heart mass, which constitutes the quantity which is important for the purposes of the monitoring action.

The monitoring signals thus obtained, where appropriate, in conjunction with other physiological parameters monitored by other sensors, not shown, may either be processed locally within the unit 3 for immediate feedback to the sensor 1 which acts as a stimulation electrode (in the typical configuration in combination with a "rate responsive" pacemaker or with a defibrillator) or may be sent to a transmission unit included in the module 3 for transmission (by means of electromagnetic waves, ultrasound, etc.) to the module 4. The signals coming from the sensor 1 (which are indicative of cardiac events such as the opening and closure of the mitral valve, the opening and closure of the aortic valve, the amount of ventricular ejection, the rapid ventricular filling or delayed ventricular filling during the atrial systole, the cardiac flow-rate, etc.) presented to the analyser 5 enable the heart function of the wearer to be monitored in real time. In particular, it is also possible to consider the incorporation in the module 3 of memory means which can record the data relating to the heart function displayed by the wearer over a certain period of time for transmission to the exterior, as a result of an interrogation made by means of the transmitter 4 during checking visits.

Moreover, it is possible to consider the direct piloting, by means of the unit 3, of a device worn by the patient for the dosed release of drugs, or the configuration of the unit 3 as an alarm unit which indicates to the patient (or to a medical team supervising the patient, even remotely) the fact that some parameters of the heart function are to be considered anomalous and/or such as to require intervention.

Conversely, the analyser 5 and the module 4 may also be used for programming functions so as to send to the module 3 indications relating to the modification of the behaviour of the module 3 and of the system of which it forms part.

EXAMPLE OF THE APPLICATION OF THE INVENTION

Figure 3:
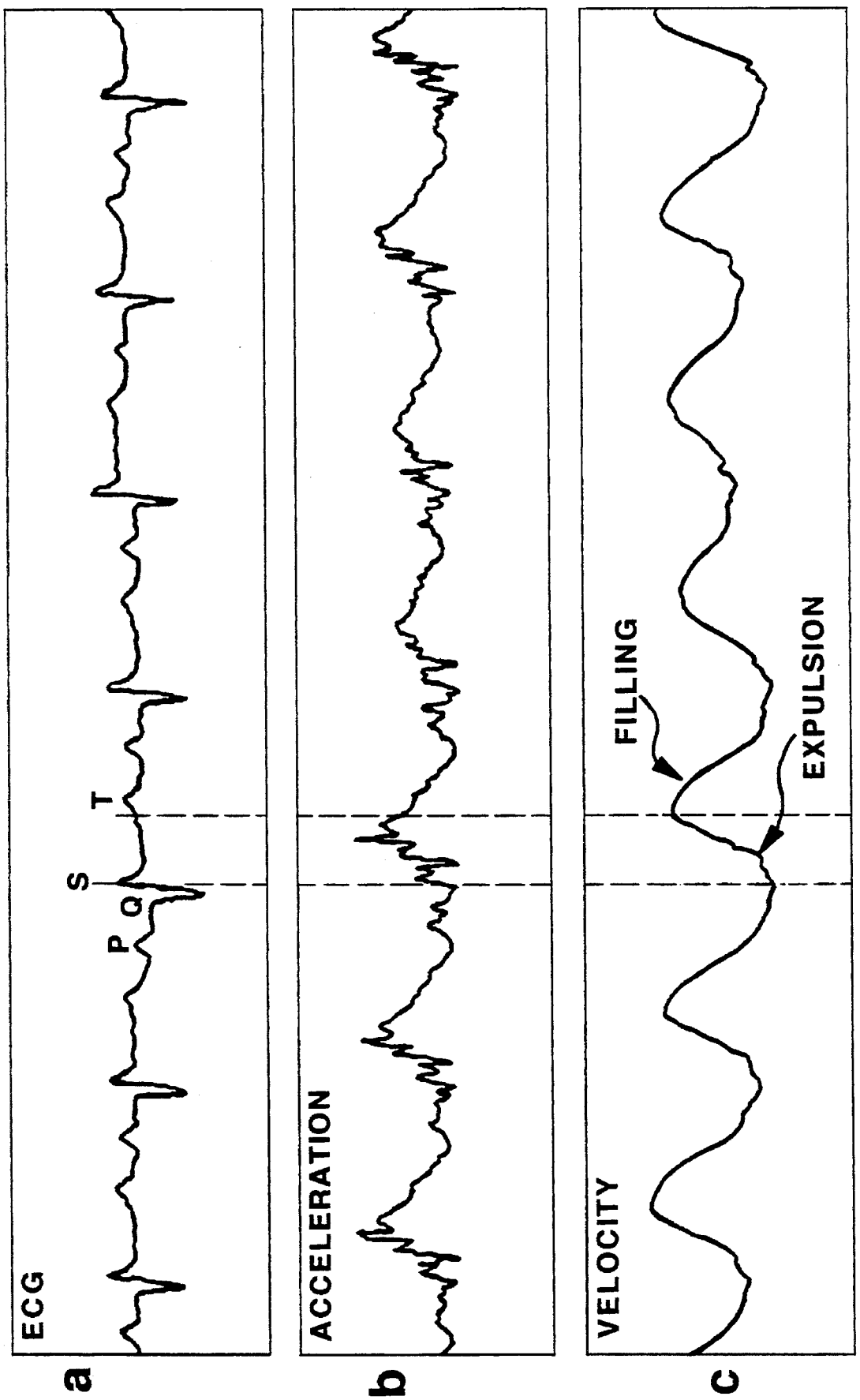

Acute recordings were made on animals by positioning an accelerometric sensor 1 in the right ventricle so as to maximize the signal due to the movements of the cardiac masses and transmitting the signal obtained, by telemetry. The integral of the signal, which is representative of the velocity curve associated with new cardiac events, is given in the time graph of FIG. 3c in comparison with homologous signals (that is, relating to the same events and related to the same time scale on the abscissa) expressed in the form of an electrocardiographic trace (the graph of FIG. 3a) and of an accelerometric signal (the graph of FIG. 3b).

It can readily be seen that the velocity signal permits macroscopic observation of the main phases corresponding to the total aortic flow and to the diastolic filling in correspondence with the events monitored by the electrocardiographic signal, taking account of the delay of mechanical contraction with respect to the electrical activation.

It should be noted that the wave of the electrical activation of the ventricles is that defined as the QRS wave. The expulsion of the blood starts from this wave and lasts until the repolarisation wave T. After the wave T is the diastolic ventricle-filling phase.

What is claimed is:

1. A device for monitoring heart function comprising:
   sensor means for monitoring at least one of momentum and velocity of a heart mass, the sensor means being adapted for positioning in correspondence with a region of the heart mass which is exposed to a contractile movement of the heart;
   means operably connected to the sensor means for generating a monitoring signal indicative of heart activity; and
   means for eliminating from the monitoring signal a component of the signal which is inherent in the contractile movement of the heart mass.

2. A method for monitoring heart activity based upon the momentum or velocity of the heart mass comprising:
   implanting a sensor within a patient's body;
   sensing at least one of acceleration, momentum and velocity of the heart mass;
   generating a signal indicative of at least one of velocity and momentum of the heart mass; and
   processing the signal to provide data indicative of heart activity.

3. The method of claim 2 further comprising transmitting the signal to a receiver located externally of the patient's body.

4. The method of claim 2 wherein the step of processing comprises processing the signal to produce data indicative of at least one of opening of the mitral valve, closure of the mitral valve, opening of the aortic valve, closure of the aortic valve, an amount of ventricular ejection, rapid ventricular filling, delayed ventricular filling during atrial systole, and cardiac flow rate.

5. The method of claim 2 wherein the implanting step comprises implanting the sensor in a region of the heart mass of low contractile activity.

6. The method of claim 5 wherein the step of implanting comprises implanting the sensor in a region of the heart mass corresponding with the intraventricular septum.

7. The method of claim 5 wherein the implanting step comprises implanting the sensor in a region of heart mass corresponding with the atrioventricular septum.

8. The method of claim 2 wherein the implanting step comprises implanting the sensor in a region of the heart mass exposed to contractile movement.

9. The method of claim 8 further comprising eliminating from the signal components of the signal which are inherent in the contractile movement of the heart mass.

10. The method of claim 2 further including storing the data indicative of heart activity.

11. A method of providing therapy to a patient comprising:
    implanting a sensor within the patient's body;
    sensing at least one of acceleration, momentum and velocity of the patient's heart mass;
    generating a signal indicative of at least one of velocity and momentum of the heart mass;
    processing the signal to provide data indicative of heart activity; and
    providing therapy to the patient based upon the patient's heart activity.

12. The method of claim 11 further comprising transmitting the signal to a receiver located externally of the patient's body.

13. The method of claim 11 wherein the processing step comprises processing the signal to provide data indicative of at least one of opening of the mitral valve, closure of the mitral valve, opening of the aortic valve, closure of the aortic valve, an amount of ventricular ejection, rapid ventricular filling, delayed ventricular filling during atrial systole, and cardiac flow rate.

14. The method of claim 11 wherein the step of implanting comprises implanting the sensor in a region of the heart mass with low contractile activity.

15. The method of claim 14 wherein the step of implanting comprises implanting the sensor in a region of the heart mass corresponding with the intraventricular septum.

16. The method of claim 14 wherein the implanting step comprises implanting the sensor in a region of the heart mass corresponding with the atrioventricular septum.

17. The method of claim 11 wherein the implanting step comprises implanting the sensor in a region of the heart mass which is exposed to contractile movement.

18. The method of claim 17 further comprising eliminating from the signal components of the signal which are inherent in the contractile activity of the heart mass.

19. The method of claim 11 wherein the step of providing therapy comprises providing electrical stimulation to the heart with a pacemaker.

20. The method of claim 11 wherein the step of providing therapy comprises providing electrical stimulation to the heart with a defibrillator.

21. The method of claim 11 wherein the step of providing therapy comprises providing a dosed release of a drug to the patient.

22. The method of claim 11 further comprising storing the data indicative of heart activity.

23. A device for monitoring a patient's heart activity based upon the momentum or velocity of the patient's heart mass comprising:

means for sensing at least one of acceleration, momentum, and velocity of the patient's heart mass;

means operably coupled to the sensing means for generating a signal indicative of at least one of momentum and velocity of the heart mass;

means for transmitting the signal;

means for receiving the signal; and means for processing the signal to provide an indication of heart activity.

24. The device of claim 23 wherein the means for sensing, generating and transmitting are sized to be implanted in the patient's body.

25. The device of claim 23 wherein the processing means provides an indication of at least one of opening of the mitral valve, closure of the mitral valve, opening of the aortic valve, closure of the aortic valve, an amount of ventricular ejection, rapid ventricular filling, delayed ventricular filling during atrial systole, and cardiac flow rate.

26. The device of claim 23 wherein the sensing means is sized for implantation in a region of the heart mass with low contractile activity.

27. The device of claim 26 wherein the sensing means is sized for implantation in a region of the heart mass corresponding to the intraventricular septum.

28. The device of claim 26 wherein the sensing means is sized for implantation in a region of the heart mass corresponding to the atrioventricular septum.

29. The device of claim 23 wherein the sensing means is sized for implantation in a region of the heart mass which is exposed to contractile movement.

30. The device of claim 29 further including means for eliminating from the signal components of the signal which are inherent in the contractile activity of the heart mass.

31. A device for providing therapy to a patient comprising:

means for sensing at least one of acceleration, momentum and velocity of the patient's heart mass;

means operably coupled to the sensing means for generating a signal indicative of at least one of momentum and velocity of the heart mass;

means for processing the signal to provide data indicative of heart activity; and means for providing therapy to the patient based upon the patient's heart activity.

32. The device of claim 31 further including means for transmitting the signal to a receiver located externally of the patient's body.

33. The device of claim 31 wherein the means for sensing, generating, processing and providing are sized to be implanted within the patient's body.

34. The device of claim 33 wherein the means for sensing, generating and processing are combined in one implantable unit.

35. The device of claim 31 further including means for transmitting the signal and means for receiving the signal.

36. The device of claim 35 wherein the transmitting means is sized to be implanted within the patient's body and the receiving means is adapted to be located external of the patient's body.

37. The device of claim 31 wherein the processing means provides data indicative of at least one of opening of the mitral valve, closure of the mitral valve, opening of the aortic valve, closure of the aortic valve, an amount of ventricular ejection, rapid ventricular filling, delayed ventricular filling during atrial systole, and cardiac flow rate.

38. The device of claim 31 wherein the sensing means is sized for implantation in a region of the heart mass with low contractile activity.

39. The device of claim 38 wherein the sensing means is sized for implantation in a region of the heart mass corresponding to the intraventricular septum.

40. The device of claim 38 wherein the sensing means is sized for implantation in a region of the heart mass corresponding to the atrioventricular septum.

41. The device of claim 31 wherein the sensing means is sized for implantation in a region of the heart mass which is exposed to contractile movement.

42. The device of claim 41 further including means for eliminating from the signal components of the signal which are inherent in the contractile activity of the heart mass.

43. The device of claim 31 wherein the means for providing therapy is a pacemaker.

44. The device of claim 31 wherein the means for providing therapy is a defibrillator.

45. The device of claim 31 wherein the means for providing therapy is a device for providing a dosed release of drug to the patient.

46. A system for monitoring a patient's heart activity based upon the momentum or velocity of the patient's heart mass comprising:

a sensor of at least one of acceleration, momentum, and velocity of the patient's heart mass;

a signal generator coupled to the sensor to provide a signal indicative of at least one of momentum and velocity of the heart mass;

a transmitter connected to the signal generator and operative to transmit the signal;

a signal receiver for receiving the signal; and a signal processor connected to receive the signal from the receiver.

47. The system of claim 46 wherein the signal processor provides an indication of at least one of opening of the mitral valve, closure of the mitral valve, opening of the aortic valve, closure of the aortic valve, an amount of ventricular ejection, rapid ventricular filling, delayed ventricular filling during atrial systole, and cardiac flow rate.

48. The system of claim 46 further including a filter to eliminate from the signal components of the signal which are inherent in the contractile activity of the heart mass.

49. A device for providing therapy to a patient comprising:

a sensor of at least one of acceleration, momentum and velocity of the patient's heart mass;

a signal generator coupled to the sensor to provide a signal indicative of at least one of momentum and velocity of the heart mass;

a signal processor connected to receive the signal and provide an output indicative of heart activity; and a therapy dispensing element responsive to the output of the signal processor to provide therapy to the patient.

50. The device of claim 49 further including a transmitter operative to transmit the signal to a receiver located externally of the patient's body.

51. The device of claim 49 wherein the signal processor provides data indicative of at least one of opening of the mitral valve, closure of the mitral valve, opening of the aortic valve, closure of the aortic valve, an amount of ventricular ejection, rapid ventricular filling, delayed ventricular filling during atrial systole, and cardiac flow rate.

52. The device of claim 49 further including a filter to eliminate from the signal components of the signal which are inherent in the contractile activity of the heart mass.

53. The device of claim 49 wherein the therapy dispensing element is a pacemaker.

54. The device of claim 49 wherein the therapy dispensing element is a defibrillator.

55. The device of claim 49 wherein the therapy dispensing element is a device for providing a dosed release of drug to the patient.

* * * * *

UNITED STATES PATENT AND TRADEMARK OFFICE
CERTIFICATE OF CORRECTION

PATENT NO.   : 5,454,838
DATED         : October 3, 1995
INVENTOR(S) : Franco Vallana et al.

It is certified that error appears in the above-identified patent and that said Letters Patent is hereby corrected as shown below:

Column 3, line 3, replace "$Q=\int_V \rho(r) \cdot u(r) dV$" with --$\vec{Q} = \int_V \rho(\vec{r}) \cdot \vec{u}(\vec{r}) dV$--; line 7, replace "$\vec{u}(\vec{r})$" with --$\vec{u}(\vec{r})$--; line 8, replace "$\rho(\vec{r})$" with --$\rho(\vec{r})$--; line 9, replace "r" with --$\vec{r}$--; line 14-15, replace "$m_1 \cdot \vec{v}_1$" with --$m_1 \cdot \vec{v}_1$--; line 18, replace "$m_2 \vec{v}_2$" with --$m_2 \vec{v}_2$--; line 21, replace "$m_2 \vec{v}_2 = -m_1 \vec{v}_1$" with --$m_2 \vec{v}_2 = -m_1 \vec{v}_1$--; line 23, replace "$\vec{v}_2$" with --$\vec{v}_2$--; line 32, replace "$F_t = M\frac{dv}{dt} - u\frac{dM}{dt}$" with --$\vec{F}_t = M\frac{d\vec{v}}{dt} - \vec{u}\frac{dM}{dt}$--; line 34, replace "$\vec{F}_t$" with --$\vec{F}_t$--; line 35, replace "v" with --$\vec{v}$--; line 36, replace "u" with --$\vec{u}$--; line 43, replace "$F_t = M\frac{dv}{dt} - u^2 \Sigma \rho$" with --$\vec{F}_t = M\frac{d\vec{v}}{dt} - u^2 \Sigma \rho$--; line 48, replace "$\vec{F}_t$" with --$\vec{F}_t$--.

Signed and Sealed this

Twentieth Day of June, 2000

*Attest:*

Q. TODD DICKINSON

*Attesting Officer*          *Director of Patents and Trademarks*